United States Patent [19]

Takeuchi et al.

[11] Patent Number: 5,170,667
[45] Date of Patent: Dec. 15, 1992

[54] METHOD AND APPARATUS FOR MONITORING STATE OF POLYMERIC MATERIALS

[75] Inventors: Shinichi Takeuchi, Tokyo; Ryohei Motegi, Hiratsuka, both of Japan

[73] Assignee: Tokimec, Inc., Tokyo, Japan

[21] Appl. No.: 621,432

[22] Filed: Dec. 4, 1990

[30] Foreign Application Priority Data

Dec. 8, 1989 [JP] Japan .................................. 1-319983
Dec. 8, 1989 [JP] Japan .................................. 1-319984

[51] Int. Cl.⁵ .............................................. G01N 9/24
[52] U.S. Cl. .......................................... 73/597; 73/599
[58] Field of Search ................. 73/594, 597, 599, 602, 73/645

[56] References Cited

U.S. PATENT DOCUMENTS

| | | | |
|---|---|---|---|
| 4,312,228 | 1/1982 | Wohltjen | 73/599 |
| 4,335,613 | 6/1982 | Luukkala | 73/599 |
| 4,754,645 | 7/1988 | Piche et al. | 73/599 |

Primary Examiner—Louis Arana
Attorney, Agent, or Firm—Wenderoth, Lind & Ponack

[57] ABSTRACT

An ultrasonic wave is emitted from an ultrasonic wave transducer for transmission to polymeric materials and received by an ultrasonic wave transducer for reception arranged at a predetermined distance away from the transducer for transmission. A propagation time of the ultrasonic wave and the level of the reception wave are measured during the process to heat or cool the polymeric materials. A state of the polymeric materials is discriminated on the basis of a characteristic curve which is determined by the propagation time and the reception wave level of the ultrasonic wave. In the case of measuring an asphalt paved road, when shoulder characteristics appear on the characteristic curve which is determined by the propagation time of the ultrasonic wave and the reception wave level, it is determined that a solid state in which a traffic lane can be opened was obtained.

6 Claims, 7 Drawing Sheets

METHOD AND APPARATUS FOR MONITORING STATE OF POLYMERIC MATERIALS

BACKGROUND OF THE INVENTION

The present invention relates to a method and apparatus for monitoring a state of polymeric materials, in which a state of polymeric materials such as plastics, rubber, asphalt, or the like depending on a temperature change is monitored by using propagation characteristics of an ultrasonic wave and, more particularly, to a monitoring method and apparatus for measuring a degree of solidification of an asphalt paved road after completion of a paving construction by using the propagation characteristics of the ultrasonic wave.

Hitherto, in polymeric materials such as a synthetic resin or the like, a discrimination as to whether or not the polymeric materials have reached a solid state due to a decrease in temperature from a viscous liquid state due to a heating process and have been changed to a state having sufficient usable practical strength or not is effected by monitoring a temperature of an object to be measured or the passage of time.

However, in the case of monitoring the temperature, since a temperature distribution in an object to be measured is ordinarily not uniform, the monitoring is executed by merely measuring a local temperature and it is difficult to accurately determine the temperature of the object. On the other hand, in the case of monitoring by the time, there is a problem such that there is a large variation of an object to be measured depending on environmental conditions such as temperature, humidity, and the like, so that the monitoring becomes unstable.

On the other hand, in the case of asphalt pavement, a traffic lane can be opened and restarted in a short time after completion of the paving construction as compared with the case of a cement concrete pavement. However, there is a problem in that if the traffic lane is opened too early, the road surface is deformed after the traffic lane was opened because the asphalt pavement was not yet completely solidified. In addition, if a traffic lane shut-off time is set to a too long time, a problem such as a traffic jam or the like occurs. Therefore, it is necessary to open the traffic lane at a proper timing.

Hitherto, as a method of determining the timing to open the traffic lane of the road which was shut off for construction, a method of determining such timing by measuring the surface temperature of the paved road has been known. That is, since it is known that the surface temperature at which the traffic lane can be opened is set to a temperature within a range from 40° to 50° C., the opening of the traffic is instructed, for instance, when the surface temperature of the road is equal to or lower than 45° C. On the other hand, a method whereby a part of the road surface is mechanically pressurized and permission or inhibition of the opening of the traffic lane is determined by checking an amount of depression of the road surface is also used.

However, the surface temperature and the internal temperature of the paved road differ. Such a temperature difference largely depends on the kind of asphalt used, the kind of crushed stones to be mixed and its mixing amount, and environmental conditions such as outside atmospheric temperature, humidity, cooling method of the road surface, and the like. Therefore, even if the surface temperature has decreased to a predetermined temperature such as 45° C. or lower, there is a case where a deep portion of the road is still held at a high temperature and the asphalt is not sufficiently hardened. There is a fear such that if the permission or inhibition of the opening of the traffic lane is unconditionally decided on the basis of the surface temperature of the paved road, the road surface will be deformed after the traffic was opened. On the other hand, in the case of the method whereby a part of the road surface is mechanically pressurized and such a determination is performed on the basis of an amount of depression, there is a problem such that a damage remains on the road surface after completion of the inspection and it is necessary to repair the road surface.

SUMMARY OF THE INVENTION

It is an object of the present invention to provide a state monitoring method of polymeric materials which can determine a state of polymeric materials depending on a temperature change by using an ultrasonic wave.

Another object of the invention is to provide a state monitoring apparatus of polymeric materials which can determine a state of polymeric materials depending on a temperature change by using an ultrasonic wave.

Still another object of the invention is to provide a state monitoring method of an asphalt paved road which can determine a degree of solidification of the asphalt paved road by using an ultrasonic wave.

Another object of the invention is to provide a state monitoring apparatus of an asphalt paved road which can determine a degree of solidification of the asphalt paved road by using an ultrasonic wave.

According to state monitoring method and apparatus of polymeric materials of the invention, processes are executed by the following procedure. First, an ultrasonic wave is emitted from an ultrasonic wave transducer for transmission to polymeric materials to be measured and is received by an ultrasonic wave transducer for reception installed at a position away from the ultrasonic wave transducer for transmission by a predetermined distance. Then, in the process of heating or cooling the polymeric materials, a propagation time of the ultrasonic wave and a level of the reception wave are measured. A state of the polymeric materials is determined on the basis of the characteristic curve which is decided by the propagation time of the ultrasonic wave and the reception wave level.

That is, the propagation time of the ultrasonic wave and the reception wave level directly reflect a viscosity and elastic characteristics of the polymeric materials which depend on the temperature. Therefore, for instance, while the characteristic curve which is determined by the propagation time and the reception wave level is monitored at a softening point of the polymeric materials, a characteristic point at which a change tendency of the curve changes appears. Thus, the state of the polymeric materials for a temperature change can be accurately known.

On the other hand, according to method and apparatus for monitoring a state of a degree of solidification of an asphalt paved road of the invention, processes are executed in the following procedure.

First, an ultrasonic wave transducer for transmission and an ultrasonic wave transducer for reception are arranged on the road surface after completion of the asphalt paving construction so as to be away from each other by a predetermined distance. Then, an ultrasonic wave is emitted from the ultrasonic wave transducer for transmission. A propagation time from when the emitted ultrasonic wave is propagated in the asphalt paved portion until it reaches the ultrasonic wave transducer for reception and a level of the reception wave are measured. When shoulder characteristics appear on a characteristic curve which is determined by the propagation time of the ultrasonic wave and the reception wave level, it is determined that a solid state in which the traffic lane can be opened was obtained.

Further, if the result of the discrimination based on the shoulder characteristics was obtained, an instruction to open the traffic lane which has been shut off for the purpose of the asphalt paving construction is displayed on a display apparatus.

That is, the propagation time of the ultrasonic wave and the reception wave level depend on the viscosity and the elastic characteristics of the asphalt portion. Therefore, when the asphalt is cooled and sufficiently hardened, what are called shoulder characteristics such that even if the propagation time changes, the reception level hardly changes appear on the characteristic curve indicative of the relationship between the propagation time and the reception level in association with a transition of the physical characteristics such as viscosity, elasticity, and the like. Accordingly, if the shoulder characteristics appeared during the measurement of the propagation time and the reception level, it is possible to determine that an enough solid state in which the traffic can be opened was obtained. For instance, an instruction to open the traffic lane is output to the display apparatus. Thus, the paved road surface is not damaged and the problem such that an instruction to open the traffic is generated in a state in which the inside of the asphalt paved road is not sufficiently hardened as in the case of the surface temperature measuring method is solved.

The above and other objects, features, and advantages of the invention will become more apparent from the following detailed description in conjunction with the accompanying drawings.

DETAILED DESCRIPTION OF THE PREFERRED EMBODIMENTS

Figure 1:
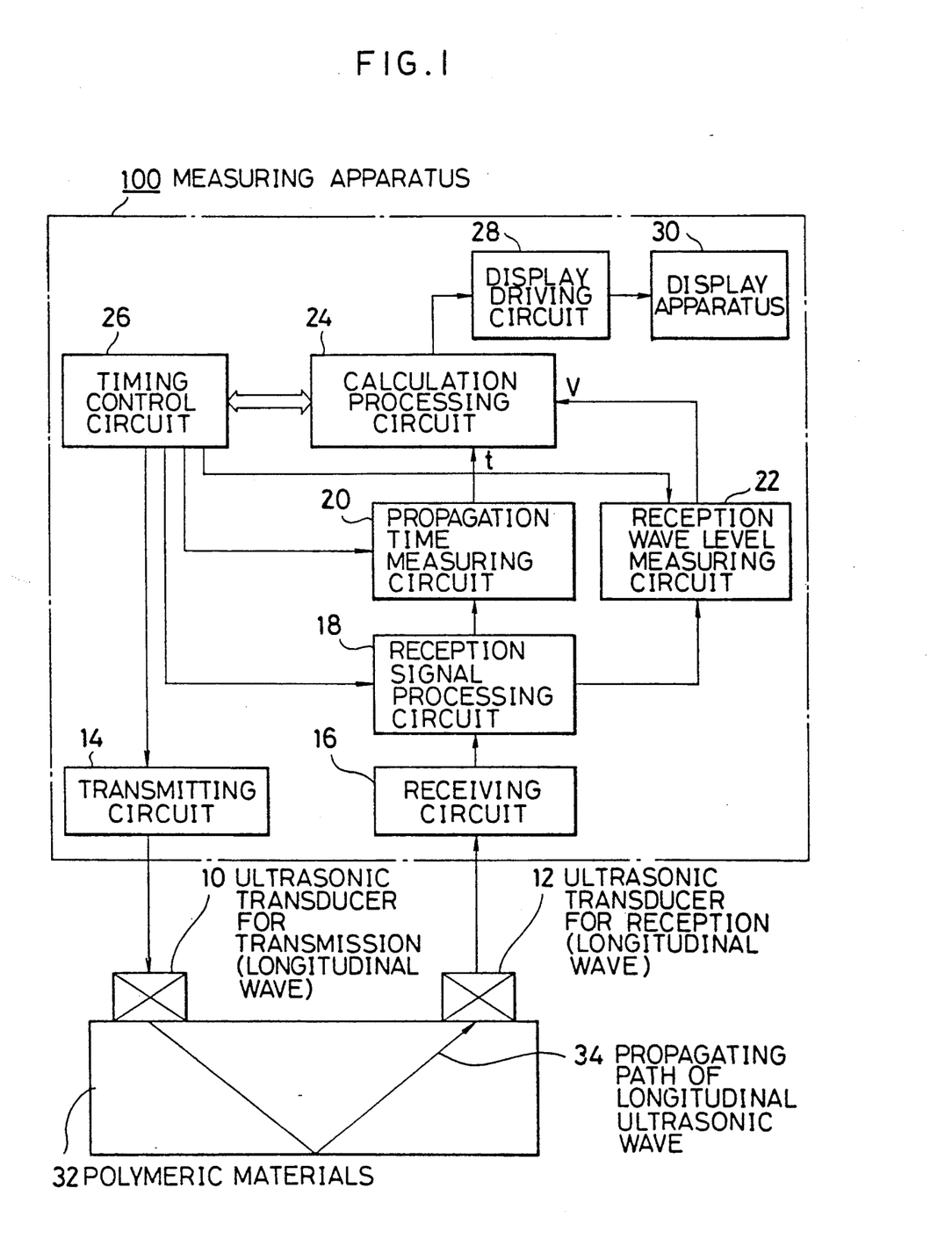
FIG. 1 is a block diagram of an embodiment of the invention.

In FIG. 1, reference numeral 10 denotes an ultrasonic wave transducer for transmission of a longitudinal ultrasonic wave and element 12 is an ultrasonic wave transducer for reception of a longitudinal ultrasonic wave. The ultrasonic wave transducer 10 for transmission and the ultrasonic wave transducer 12 for reception are arranged at a predetermined distance at positions which are come into contact with polymeric materials 32 to be measured. For instance, in the case of monitoring the state of the resin in the die of an injection molding machine, the transducer 10 for transmission and the transducer 12 for reception are assembled at predetermined positions in the die so as to directly or indirectly come into contact with a resin.

An ultrasonic wave drive signal is supplied to the transducer 10 for transmission from a transmitting circuit 14 provided in a measuring apparatus 100, so that the transducer 10 emits a longitudinal ultrasonic wave to the polymeric materials 32. The ultrasonic wave emitted into the polymeric materials 32 passes through an ultrasonic wave propagating path 34 which reflects the ultrasonic wave on the side opposite to the incident side. Then, the reflected ultrasonic wave is received by the transducer 12 for reception and is converted into an electrical signal. After that, the electrical signal is amplified by a receiving circuit 16 provided in the measuring apparatus 100. An output of the receiving circuit 16 is fed to a reception signal processing circuit 18. The processing circuit 18 eliminates noise from the reception signal and, thereafter, A/D converts the reception signal and stores the waveform data.

A propagation time measuring circuit 20 measures a time from a time point of a transmission trigger from a timing control circuit 26 to a time point when the reception waveform stored in the reception signal processing circuit 18 is obtained, that is, a propagation time t from a time point when the transducer 10 for transmission emitted an ultrasonic wave to the polymeric materials 32 to a time point when the emitted ultrasonic wave was received by the transducer 12 for reception.

A reception wave level measuring circuit 22 measures a peak amplitude value of the reception waveform data stored in the processing circuit 18 as a reception wave level V.

A calculation processing circuit 24 transmits a transmission/reception control to the timing control circuit 26 and extracts the propagation time t regarding the reception wave obtained in association with the transmission/reception control from the propagation time measuring circuit 20. Further, the calculation processing circuit 24 extracts the reception wave level V from the reception wave level measuring circuit 22 and forms a characteristic curve which is determined by the propagation time t and the reception wave level V and outputs it.

Then, the principle of the monitoring of the state of the polymeric materials using the ultrasonic wave according to the invention will be described.

Figure 2:
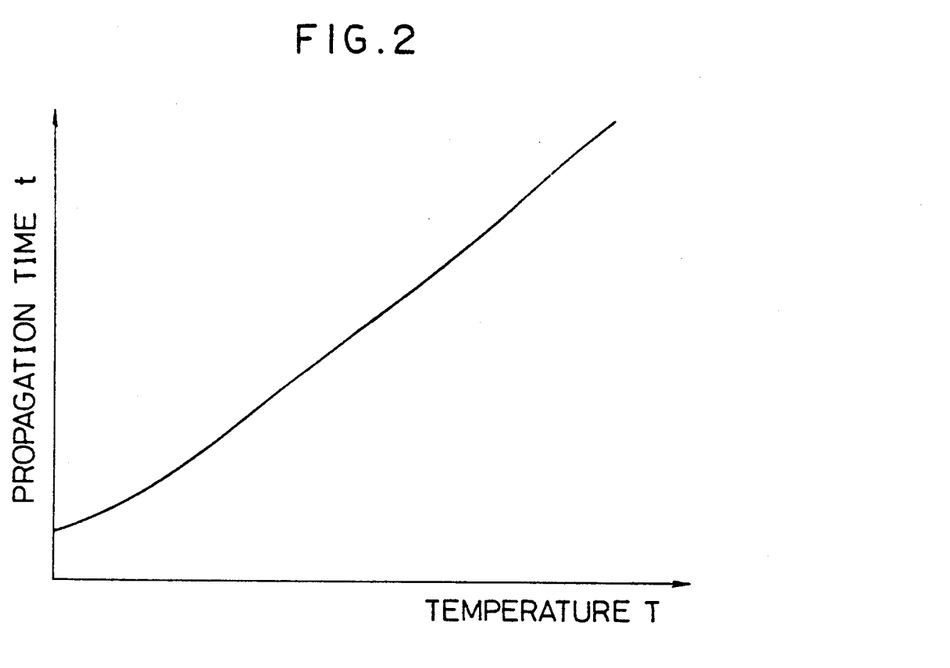
FIG. 2 is a characteristic diagram showing the relationship between the temperature of polymeric materials and the propagation time of an ultrasonic wave.

FIG. 2 is a characteristic diagram showing the relationship between a temperature T of the polymeric materials and the ultrasonic wave propagation time t. As will be obviously understood from the diagram, there is a relationship such that the ultrasonic wave propagation time t almost linearly increases with an increase in temperature T.

Figure 3:
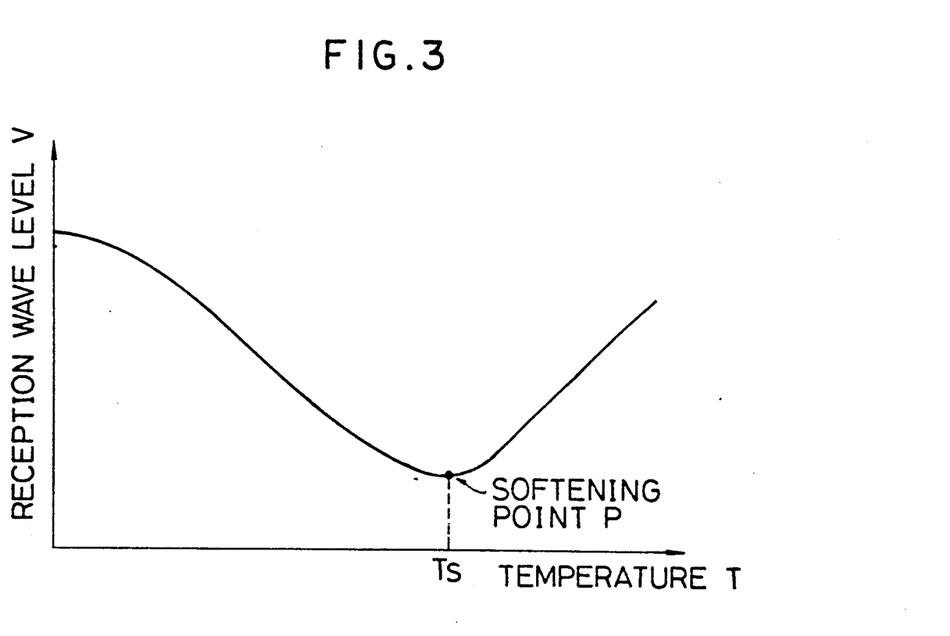
FIG. 3 is a characteristic diagram showing the relationship between the temperature of polymeric materials and the reception wave level of an ultrasonic wave.

On the other hand, FIG. 3 shows the relationship of the reception wave level (peak value or amplitude value) V of the ultrasonic wave to the temperature of the polymeric materials. When the temperature T is raised from a state in which the polymeric materials are solid in FIG. 3, the reception wave level V almost linearly decreases. As the temperature T approaches a softening point P, a decrease in reception wave level is reduced. When the temperature exceeds the softening point P, the reception wave level linearly increases.

A temperature $T_s$ of the softening point P is set to a value about 95° C., for instance, in the case of polymethylmethacrylate (acrylic resin).

The characteristics of the reception wave level V to the temperature T in FIG. 3 are based on the experimental data obtained in the case where a test block of polymeric materials is put into a thermostatic bath and is heated to a set temperature and, thereafter, it is cooled. That is, they are the characteristics which are obtained in the case where a relatively thick polymeric block was cooled so as to have a uniform thickness as a whole. However, in the actual polymeric materials, since the surface temperature differs from the internal temperature during the cooling operation, the characteristics as shown in FIG. 3 are not directly obtained. However, according to the experiments, it has been confirmed that even if the surface temperature differs from the internal temperature, the shape itself of the characteristic curve shown in FIG. 3 does not change but the curve is merely shifted in the direction of the temperature axis.

Figure 4:
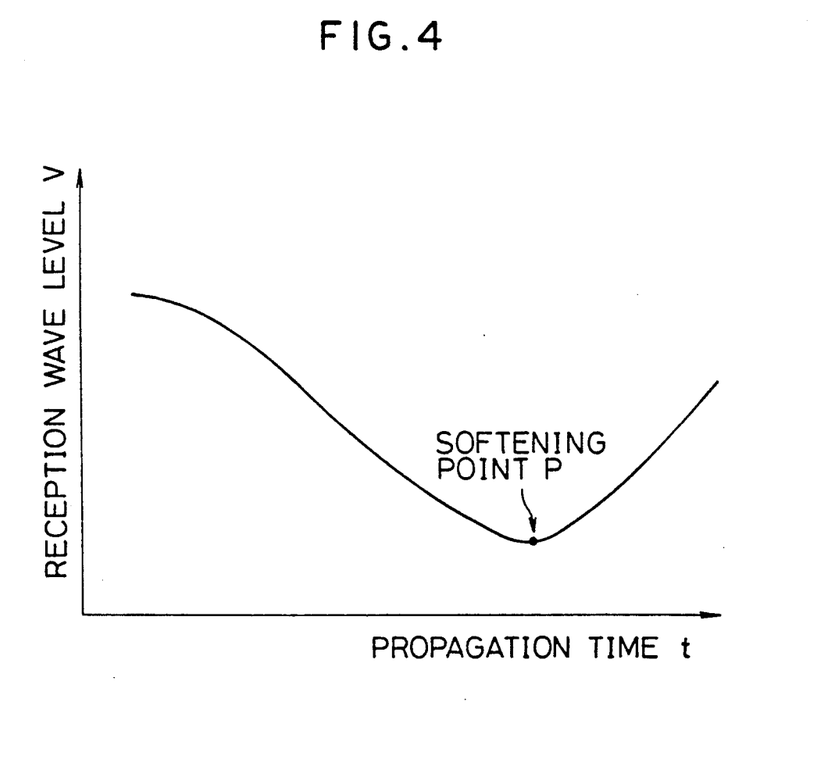
FIG. 4 is a characteristic diagram showing the relation between the propagation time of an ultrasonic wave having shoulder characteristics which are used to determine a degree of solidification and the reception wave level of the invention.

FIG. 4 is a characteristic diagram showing the relationship of the reception wave level V to the propagation time t by erasing the temperature T which is common to both of the characteristics shown in FIGS. 2 and 3 on the basis of the characteristics between the temperature T and the propagation time t shown in FIG. 2 and the characteristics between the temperature T and the reception wave level V shown in FIG. 3. The characteristic curve of FIG. 4 is used to determine the state of the polymeric materials of the invention shown in FIG. 1.

In the characteristic diagram of FIG. 4, since the propagation time t of the abscissa axis is proportional to the temperature T as will be obvious from FIG. 2, the propagation time t has a value which is obtained by multiplying an inclination (constant) of a straight line shown in FIG. 2 to the temperature T. On the other hand, there is obtained a characteristic curve having a shape corresponding to the temperature T and the reception wave level V shown in FIG. 3 for a change in propagation time t.

Therefore, the calculation processing circuit 24 in the embodiment of FIG. 1 extracts both of the propagation time t which is obtained from the propagation time measuring circuit 20 and the reception wave level V which is obtained from the reception wave level measuring circuit 22 and forms the characteristic curve shown in FIG. 4. The resultant characteristic curve is sequentially electronically plotted and displayed on a display apparatus 30 through a display driving circuit 28.

In addition to the electronic plot display of the characteristic curve, the calculation processing circuit 24 forms the characteristic curve shown in FIG. 4 and the characteristic curve is not directly displayed but, at a time point when a singular point was admitted, an indication which means the arrival at the singular point can be also executed by acoustic means such as a buzzer or an optical means such as a lamp in the display apparatus 30 through the display driving circuit 28.

Figure 5:
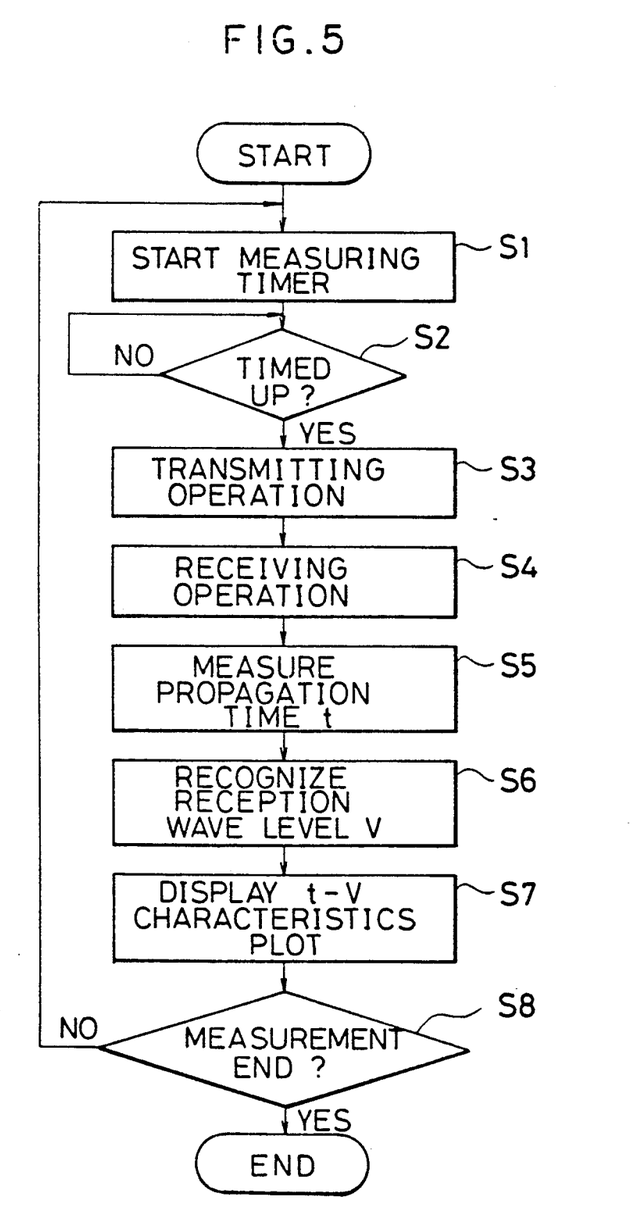
FIG. 5 is a flowchart for a measuring operation of the invention.

The state monitoring operation according to the embodiment of FIG. 1 will now be described with reference to an operation flowchart of FIG. 5.

First, prior to measuring, the ultrasonic wave transducer 10 for transmission and the ultrasonic wave transducer 12 for reception are installed at a predetermined distance in a contacting state with the polymeric materials 32 as shown in FIG. 1. When a power source of the measuring apparatus 100 is turned on in the above state, the measurement is executed in accordance with the operation flow of FIG. 5.

First, a measuring timer to decide a measuring period is started in step S1. After the measuring timer was started in step S1, a check is made in step S2 to determine whether or not the measuring timer has timed up. If YES, step S3 follows. In step S3, a transmission trigger is output from the timing control circuit 26 to the transmitting circuit 14. The transmitting circuit 14 outputs an ultrasonic wave drive signal (transmission pulse voltage) to the transducer 10 for transmission synchronously with the transmission trigger, thereby allowing a longitudinal ultrasonic wave to be emitted into the polymeric materials 32.

In the next step S4, the receiving operation is executed. In the receiving operation, the reception wave on the longitudinal wave propagating path 34 which was converted into the electric signal by the transducer 12 for reception is amplified by the receiving circuit 16. After that, the reception signal processing circuit 18 eliminates noise from the signal and A/D converts the signal. The resultant waveform data is stored.

In the next step S5, the propagation time measuring circuit 20 measures the propagation time t. In step S6, the reception wave level measuring circuit 22 measures the reception wave level V.

In step S7, the calculation processing circuit 24 reads the propagation time t and the reception wave level V and forms the characteristic curve shown in FIG. 4 and outputs and displays it (plot display). In step S7, if a characteristic change point appears in the output display of the characteristic curve and it is determined that the state of the polymeric materials has changed, step S8 follows and a check is made to see whether or not the measurement has been finished. The processes in steps S1 to S8 are repeated until the end of the measurement.

In the measurements of the propagation time t and the reception wave level V based on the transmission and reception of the ultrasonic wave in steps S3 to S6, since stable data is not obtained by the single measuring operation, it is desirable to continuously execute a plurality of transmitting and receiving operations and to display the characteristic curve in step S7 on the basis of the average value of a plurality of propagation times t and the average value of a plurality of reception wave levels V which were obtained as the results of the transmitting and receiving operations.

Figure 6:
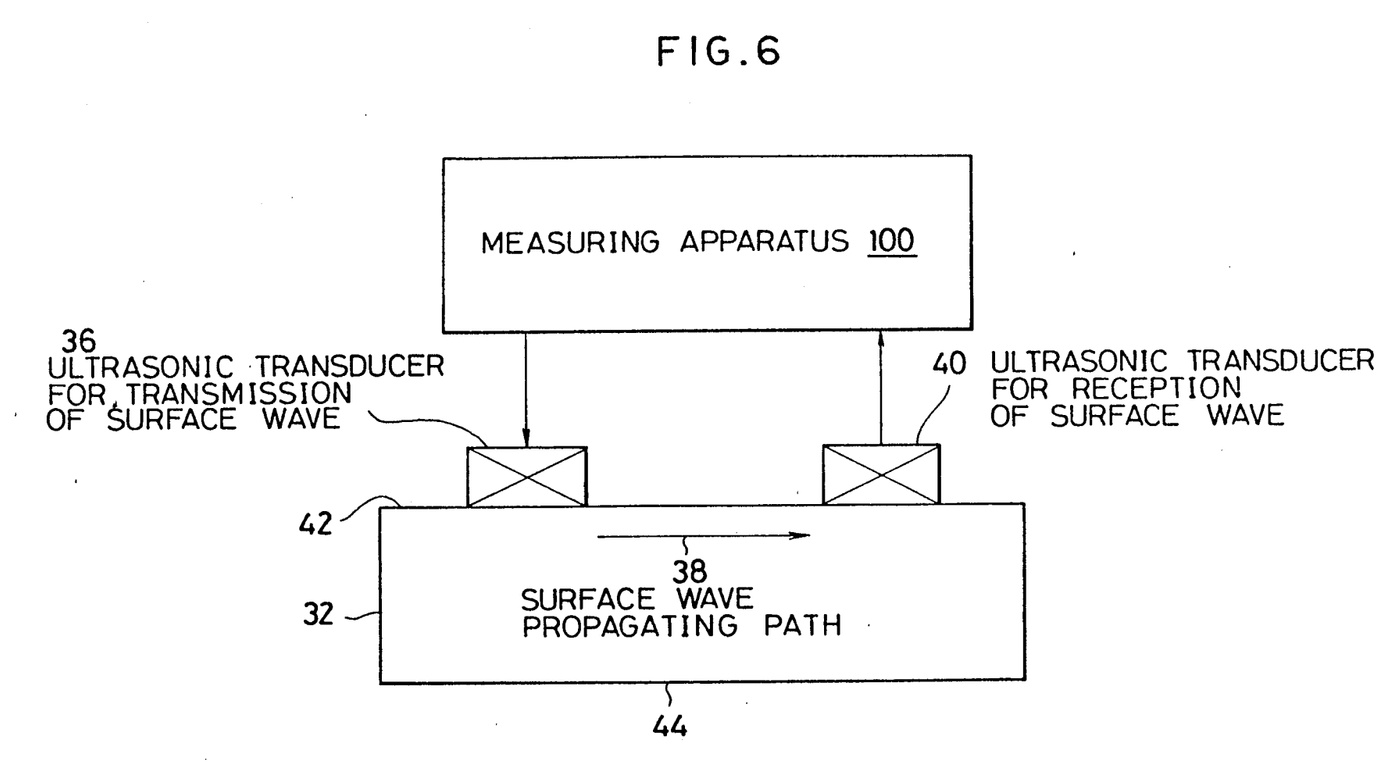
FIG. 6 is a block diagram showing another embodiment of the invention using a surface wave.

FIG. 6 is a block diagram showing another embodiment of the invention which is characterized in that the state of the polymeric materials is monitored by using ultrasonic wave transducers for transmission and reception of a surface wave.

In FIG. 6, reference numeral 36 denotes an ultrasonic wave transducer for transmission of a surface wave and element 40 is an ultrasonic wave transducer for reception of the surface wave. The transducers 36 and 40 are arranged at a predetermined distance so as to come into contact with the polymetic materials 32 prior to measuring. The measuring apparatus 100 is provided for the transducers 36 and 40. The measuring apparatus 100 has the same circuit construction as that shown in the embodiment of FIG. 1.

In the measuring operation according to the embodiment of FIG. 6, when a power source of the measuring apparatus 100 is turned on, an ultrasonic wave drive signal is output from the transmitting circuit 14 of the measuring apparatus 100 to the transducer 36 for transmission of the surface wave, so that a surface wave is excited. The surface wave is propagated in a surface wave propagating path 38 along a surface 42 of the polymeric materials 32 and arrives at the transducer 40 for reception of the surface wave. The transducer 40 converts the received surface wave into an electrical signal and feeds to the measuring apparatus 100. The propagation time t and the reception wave level V are measured in a manner similar to that of the embodiment of FIG. 1.

Although the ultrasonic wave is used in the embodiment of FIG. 6 is a surface wave, a propagation constant and an attenuation constant of the surface wave reflect the viscosity and elastic characteristics in a range until a depth of about one wavelength of the ultrasonic surface wave from the surface 42 of the polymeric materials 32. Therefore, even in the embodiment of FIG. 6 using the surface wave propagation, in a manner similar to the case of the propagation of the longitudinal ultrasonic wave shown in FIG. 1, the relationship between the temperature T and the propagation time t shown in FIG. 2 and the relationship between the temperature T and the reception wave level V shown in FIG. 3 are obtained. Thus, the relationship of the characteristic curve between the propagation time t and the reception wave level V shown in FIG. 4 is likewise derived.

In the embodiment, the systems using the longitudinal ultrasonic wave and the surface wave as ultrasonic waves which propagate in the polymeric material portion have been described as the examples. However, the invention can be also substantially similarly applied to a system using a transversal ultrasonic wave, a system using a plate wave, and a system using various elastic wave motions other than the above waves.

On the other hand, as practical examples of the state monitoring according to the invention, the invention can be applied to the monitoring of other arbitrary states of a resin in the die of a molding machine, an adhesive layer, a molding resin, a resin sealing of a structure, a surface of an asphalt paved road, and the like.

Further, as polymeric materials whose state is monitored, proper materials such as synthetic resin, asphalt, rubber, and the like can be used.

Explanation will now be made with respect to an embodiment in which an asphalt paved road after completion of the paving construction is used as an object to be measured in place of the polymeric materials 32 in FIG. 1 and a degree of solidification is measured.

Figure 8:
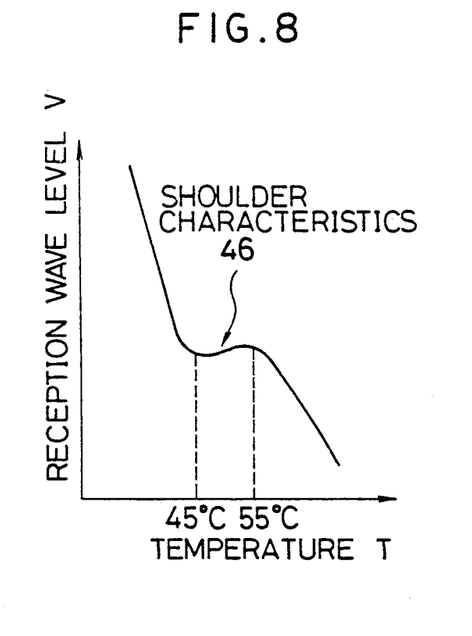
FIG. 8 is a characteristic diagram showing the relationship between the temperature of an asphalt pavement and the reception wave level of an ultrasonic wave.

FIG. 8 is a characteristic diagram showing the relationship between the temperature T of the asphalt pavement and the propagation time t of the ultrasonic wave. As will be obviously understood from the characteristic diagram, it has experimentally been confirmed that there is a relationship such that the propagation time t of the ultrasonic wave almost linearly decreases with a decrease in temperature T after completion of the asphalt construction.

Figure 9:
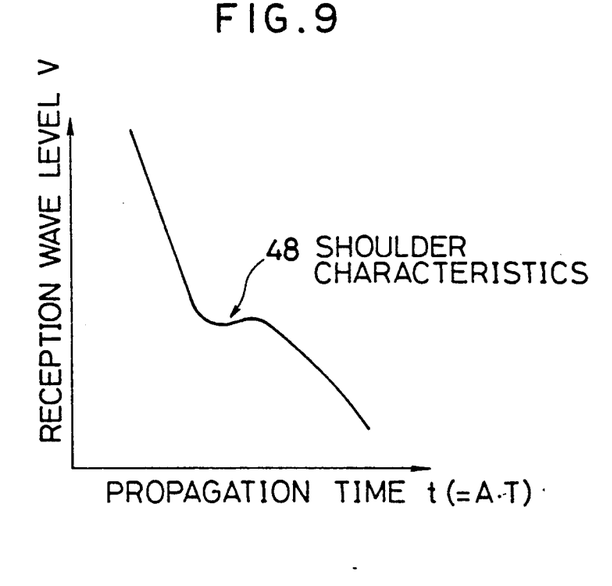
FIG. 9 is a characteristic diagram showing the relationship between the propagation time of an ultrasonic wave having shoulder characteristics which are used to determine a degree of solidification of an asphalt pavement of the invention and the reception wave level.

FIG. 9 shows the relationship of the reception wave level (peak value or amplitude value) V of the ultrasonic wave to the temperature of the asphalt pavement. In FIG. 9, when the temperature T decreases to, for example, a value near 55° C. after completion of the asphalt paving construction, the reception wave level V almost linearly increases. On the other hand, when the temperature T decreases to 55° C. or lower, the increase in reception wave level V is suppressed and is held to a value within an almost predetermined range for a period of time until the temperature decreases to 45° C. When the temperature T further decreases to 45° C. or lower, the reception wave level again linearly increases with a decrease in temperature. A change in reception wave level V is almost constant in a range of T=55° C. to 45° C. What are called shoulder characteristics 46 are obtained.

Actually, the asphalt pavement has a temperature distribution in the thickness direction. However, in this case as well, even if the surface temperature differs from the internal temperature, the shape itself of the characteristic curve having the shoulder characteristics 46 shown in FIG. 8 does not change but the curve is merely shifted in the direction of the temperature axis. It has been confirmed that the shoulder characteristics 46 are almost certainly obtained in a range near 45° C. to 55° C.

Figure 7:
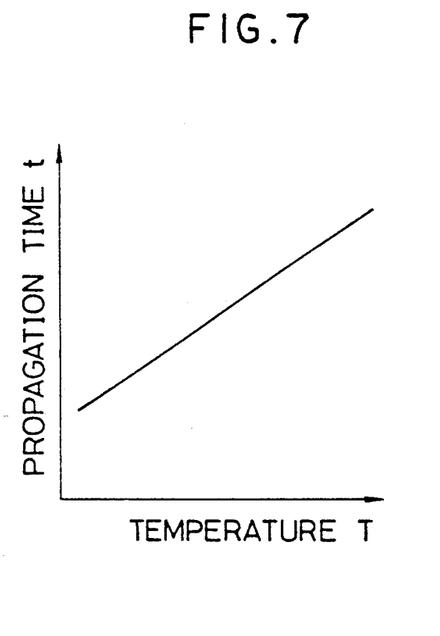
FIG. 7 is a characteristic diagram showing the relationship between the temperature of an asphalt pavement and the propagation time of an ultrasonic wave.

FIG. 9 is a characteristic diagram showing the relationship of the reception wave level V to the propagation time t which is obtained by erasing the temperature T which is common to both of the characteristics of FIGS. 7 and 8 on the basis of the characteristics between the temperature T and the propagation time t shown in FIG. 7 and the characteristics between the temperature T and the reception wave level V shown in FIG. 8. The characteristic curve of FIG. 9 is used to discriminate a degree of solidification of the asphalt pavement in the embodiment of FIG. 1.

In FIG. 9, as will be obviously understood from FIG. 7, since the propagation time t on the abscissa axis is almost proportional to the temperature T, the propagation time t has a value obtained by multiplying an inclination (constant) of the straight line shown in FIG. 7 to the temperature T. A characteristic curve having shoulder characteristics 48 corresponding to the temperature T and the reception wave level V shown in FIG. 8 is obtained for a change in propagation time t.

Therefore, the calculation processing circuit 24 in the embodiment of FIG. 1 receives both the propagation time t which is derived from the propagation time measuring circuit 20 and the reception wave level V which is derived from the reception wave level measuring circuit 22 and checks to see if the shoulder characteristics 48 of the characteristic curve shown in FIG. 9 has appeared. If it is determined that the calculation processing circuit 24 has detected the shoulder characteristics 48, an instruction to open the traffic lane is displayed by the display apparatus 30 through the display driving circuit 28.

Figure 10:
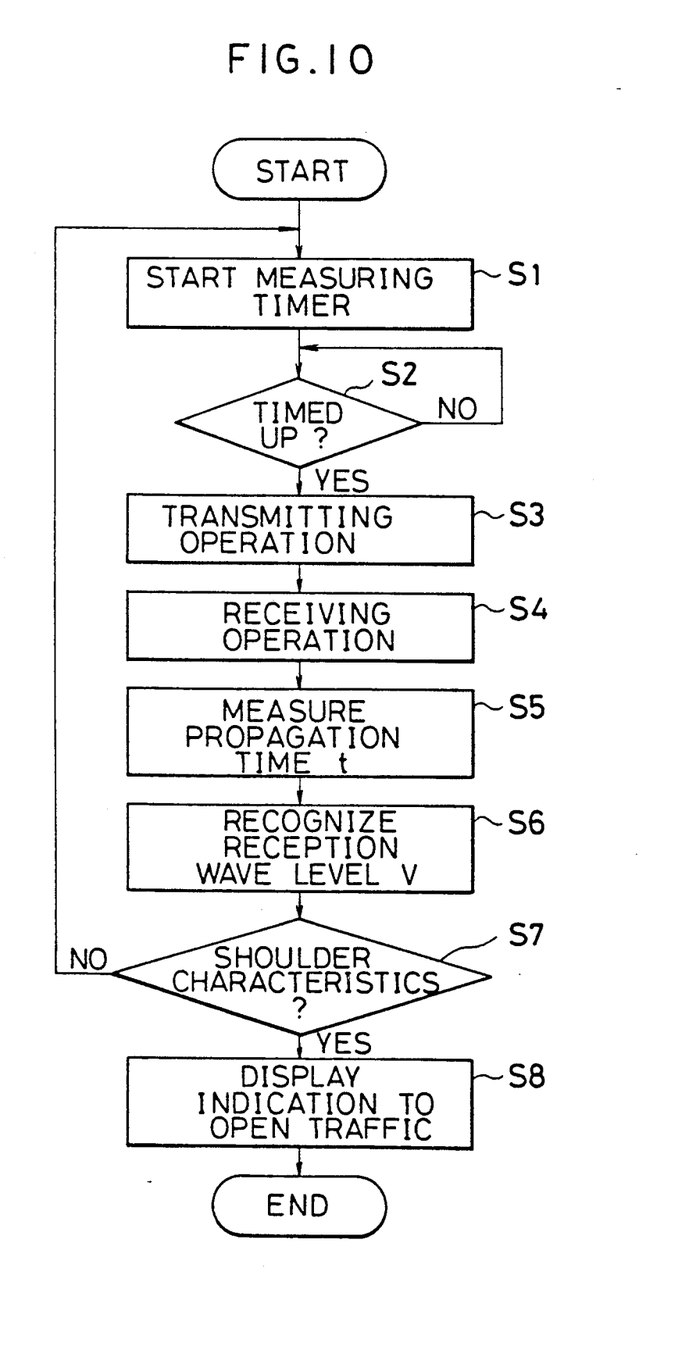
FIG. 10 is a flowchart for the operation to monitor a degree of solidification of an asphalt pavement.

The operation to measure a degree of solidification of the asphalt pavement according to the embodiment of FIG. 1 will now be described with reference to an operation flowchart of FIG. 10.

First, prior to measuring, in a manner similar to the case of the polymeric materials 32 in FIG. 1, the ultrasonic wave transducer 10 for transmission and the ultrasonic wave transducer 12 for reception are installed at a predetermined distance of e.g., 10 cm on the road surface of the asphalt pavement after completion of the asphalt paving construction. When the power source of the measuring apparatus 100 is turned on in the above state, the measurement is executed in accordance with the operation flow of FIG. 10.

First, in step S1, a measuring timer to decide a measuring period is started. A timer having a set time of, e.g., one minute is used as a measuring timer. After the measuring timer was started in step S1, a check is made in step S2 to see if the measuring timer has timed up. If the time-up has been determined one minute after the start of the measuring timer, step S3 follows and a transmission trigger is output from the timing control circuit 26 to the transmitting circuit 14. The transmitting circuit 14 outputs an ultrasonic wave drive signal (transmission pulse voltage) to the ultrasonic wave transducer 10 for transmission synchronously with the transmission trigger, thereby allowing a longitudinal ultrasonic wave to be emitted to the asphalt pavement.

In the next step S4, the receiving operation is executed. In the receiving operation, after the reception wave of the longitudinal ultrasonic wave which had been converted into an electrical signal by the ultrasonic wave transducer 12 for reception was amplified by the receiving circuit 16, the reception signal processing circuit 18 eliminates noise from the signal and executes the A/D conversion and the resultant waveform data is stored.

In step S5, the propagation time t is measured by the propagation time measuring circuit 20. In step S6, the reception wave level V is measured by the reception wave level measuring circuit 22.

In step S7, the calculation processing circuit 24 reads the propagation time t and the reception wave level V and checks to see if the shoulder characteristics 48 of the characteristic curve shown in FIG. 9 has been obtained. The determination as to the shoulder characteristics in step S7 is made in the following manner. Assuming that the propagation time and the reception wave level which were obtained at the preceding time are set to $t_{n-1}$ and $V_{n-1}$ and the propagation time and the reception wave level which are obtained at the present time are set to $t_n$ and $V_n$, $$\Delta t = t_{n-1} - t_n$$

$$\Delta V = V_{n-1} - V_n$$

are obtained and, further, a ratio of a change in reception wave level V to a change in propagation time t at the preceding and present times is calculated as $\Delta V/\Delta t$. When a state in which the value of $\Delta V/\Delta t$ is equal to or less than a predetermined value which gives the shoulder characteristics 48 continuously appeared a predetermined number of times, it is determined that the shoulder characteristics 48 were obtained.

If it is decided in step S7 that the shoulder characteristics were obtained, step S8 follows and an instruction to open the traffic lane is displayed by the display apparatus 30 through the display driving circuit 28. A series of processes are finished.

On the contrary, if the shoulder characteristics are not obtained in step S7, the processing routine is returned to step S1 and the similar measuring processes are repeated.

In the measurement of the propagation time t and the reception wave level V based on the transmitting and receiving operations of the ultrasonic wave in steps S3 to S6, since the stable data cannot be obtained by the single measuring operation, it is desirable to continuously execute the transmitting and receiving operations a plurality of times and to execute the discrimination about the shoulder characteristics in step S7 on the basis of the average value of a plurality of propagation times t and the average value of a plurality of reception wave levels V which were obtained as the results of those operations.

The ultrasonic wave transducers for transmission and reception of a surface wave shown in FIG. 6 can be also used to measure a degree of solidification of the asphalt paved road.

In the embodiment of FIG. 6 using the surface wave of the ultrasonic wave as well, the propagation constant and attenuation constant of the surface wave reflect the viscosity and elastic characteristics in a range until a depth of about one wavelength of the ultrasonic surface wave from the surface of the asphalt paved road. Therefore, even in the embodiment using the propagation of the surface wave, similarly to the case of the propagation of the longitudinal ultrasonic wave shown in FIG. 1, the relationship between the temperature T and the propagation time t shown in FIG. 7 and the relationship between the temperature T and the reception wave level V shown in FIG. 8 are obtained, so that the relationship between the propagation time t and the reception wave level V having the shoulder characteristics 48 shown in FIG. 9 is derived.

In the above embodiment, the systems using the longitudinal ultrasonic wave and the surface wave as the ultrasonic waves which propagate in the asphalt paved portion have been described as examples. However, the invention can be also substantially similarly applied to a system using a transversal ultrasonic wave, a system using a plate wave, and a system using various kinds of elastic wave motions other than those waves.

What is claimed is:

1. A method of monitoring a state of an asphalt paved road having at least one traffic lane, comprising:

a first step of arranging an ultrasonic wave transmitting means and ultrasonic wave receiving means at a predetermined distance on the surface of a road after completion of an asphalt paving construction and repetitively emitting an ultrasonic wave from said ultrasonic wave transmitting means every predetermined period of time;

a second step of repetitively measuring a transit time which is the amount of time from a time point when the ultrasonic wave generated by the ultrasonic wave transmitting means enters an asphalt pavement portion to a time point when such an ultrasonic wave has propagated through the asphalt pavement itself and has reached the ultrasonic wave receiving means and is received and also repetitively measuring a reception wave level; and a third step of determining that the asphalt paved road has reached a solid state in which a traffic lane thereof can be opened to support and allow passage of vehicles when shoulder characteristics appear on a characteristic curve which is obtained as a result of the repetitive measurement of both the transit time and the reception wave level measured in the second step.

2. A method according to claim 1, wherein the determination of the shoulder characteristics in the third step is executed in a manner such that assuming that the transit time and the reception wave level which were measured at the preceding predetermined time period are set to $t_{n-1}$ and $V_{n-1}$ and the transit time and the reception wave level which were measured at the present time period are set to $t_n$ and $V_n$, respectively, then $$\Delta t = t_{n-1} - t_n$$

$$\Delta V = V_{n-1} - V_n$$

are obtained and, further, a ratio of a change in reception wave level V for a change in transit time t at every predetermined measuring time period is obtained as $\Delta V/\Delta t$, and when a state in which the ratio between said changes is equal to or less than a predetermined value has continuously appeared a predetermined number of times, it is determined that the shoulder characteristics have been obtained.

3. A method according to claim 1, wherein in the third step, if the asphalt road has reached the solid state in which the traffic lane thereof can be opened has been determined on the basis of the shoulder characteristics, an instruction to open the traffic lane of the asphalt road which had been shut off for the asphalt paving construction is displayed by a display apparatus.

4. An apparatus for monitoring a state of an asphalt paved road having at least one traffic lane, comprising:
   an ultrasonic wave transmitting means which is arranged on the surface of the road after completion of the asphalt paving construction;
   an ultrasonic wave receiving means which is arranged at a predetermined distance away from the ultrasonic wave transmitting means;
   a transmitting driving means for repetitively driving the ultrasonic wave transmitting means every predetermined period of time, thereby allowing an ultrasonic wave to be emitted so as to enter the asphalt paved portion;
   an amplifying means for amplifying and outputting a reception signal of the ultrasonic wave receiving means;
   a transit time measuring means for repetitively measuring a transit time which the amount of time from a time point when the ultrasonic wave generated by the ultrasonic wave transmitting means enters an asphalt paved portion to a time point when such an ultrasonic wave has propagated through the asphalt pavement itself and has reached the ultrasonic wave receiving means and is received;
   a reception wave level measuring means for repetitively measuring a reception wave level of the reception wave received by the ultrasonic wave receiving means; and
   a calculation processing means for checking to see whether or not shoulder characteristics have been obtained on a characteristic curve which is obtained as a result of the repetitive measurements of both the transit time and the reception wave level of the ultrasonic wave, thereby determining that the asphalt paved road has reached a solid state in which a traffic lane thereof can be opened to support and allow passage of vehicles when the shoulder characteristics have been obtained.

5. An apparatus according to claim 4, wherein the determination of the shoulder characteristics by the calculation processing means is executed in a manner such that assuming that the transit time and the reception wave level which were measured at the preceding predetermined time period are set to $t_{n-1}$ and $V_{n-1}$ and the transit time and the reception wave level which were measured at the present predetermined time period are set to $t_n$ and $V_n$, respectively, then $$\Delta t = t_{n-1} - t_n$$

$$\Delta V = V_{n-1} V_n$$

are obtained and, further, a ratio of a change in reception wave level V to a change in transit time t at every predetermined measuring time period is obtained as $\Delta V/\Delta t$, and when a state in which the ratio between said changes is equal to or less than a predetermined value has continuously appeared a predetermined number of times, it is determined that the shoulder characteristics have been obtained.

6. An apparatus according to claim 4, wherein when the calculation processing means determines that the asphalt road has reached the solid state in which the traffic lane thereof can be opened was obtained on the basis of the shoulder characteristics, an instruction to open the traffic lane of the asphalt road which had been shut off for the asphalt paving construction is displayed by a display apparatus.

* * * * *